(12) United States Patent
Oomori et al.

(10) Patent No.: US 6,512,579 B2
(45) Date of Patent: Jan. 28, 2003

(54) DEFECT INSPECTION APPARATUS

(75) Inventors: Takeo Oomori, Hachioji (JP); Kinya Kato, Yokohama (JP)

(73) Assignee: Nikon Corporation, Tokyo (JP)

( * ) Notice: Subject to any disclaimer, the term of this patent is extended or adjusted under 35 U.S.C. 154(b) by 11 days.

(21) Appl. No.: 09/781,957

(22) Filed: Feb. 14, 2001

(65) Prior Publication Data

US 2001/0017694 A1 Aug. 30, 2001

(30) Foreign Application Priority Data

Feb. 15, 2000 (JP) ........................................ 2000-036396

(51) Int. Cl.$^7$ .............................................. G01N 21/00
(52) U.S. Cl. ................................................. 356/237.5
(58) Field of Search ........................... 356/237.1, 237.2, 356/237.3, 237.4, 237.5, 239.1, 239.3, 239.7; 250/559.4, 559.41, 559.42, 559.44, 559.45; 302/141, 144, 145

(56) References Cited

U.S. PATENT DOCUMENTS 5,428,442 A * 6/1995 Lin et al. .................. 356/237.1
6,122,046 A * 9/2000 Almogy .................... 356/237.2

FOREIGN PATENT DOCUMENTS

JP 08075661 A 3/1996

* cited by examiner

Primary Examiner—Michael P. Stafira
(74) Attorney, Agent, or Firm—Oliff & Berridge, PLC

(57) ABSTRACT

An illumination optical system for illuminating a substrate and a light receiving optical system that receives diffracted light from the wafer are provided in a defect inspection apparatus that inspects for a defect present at the wafer based upon an image of the wafer obtained at the light-receiving optical system, with a numerical aperture at the illumination optical system set different from a numerical aperture at the light-receiving optical system and the absolute value of the difference between the numerical apertures at the illumination optical system and the light-receiving optical system set at a value equal to or larger than the quantity of the angular offset manifesting between the direction along which the diffracted light advances and the direction along which an optical axis of the light-receiving optical system extends. As a result, highly reliable inspection results by preventing the contrast of an image of a substrate formed by diffracted light from becoming lowered either in its entirety or in part is achieved even when there is an angular offset between the direction in which the diffracted light from the substrate advances and the direction of the optical axis of a light-receiving system.

11 Claims, 11 Drawing Sheets

10 DEFECT INSPECTION APPARATUS
13 ILLUMINATION OPTICAL SYSTEM
14 LIGHT-RECEIVING OPTICAL SYSTEM

DIRECTION ALONG WHICH PLANE OF INCIDENCE EXTENDS

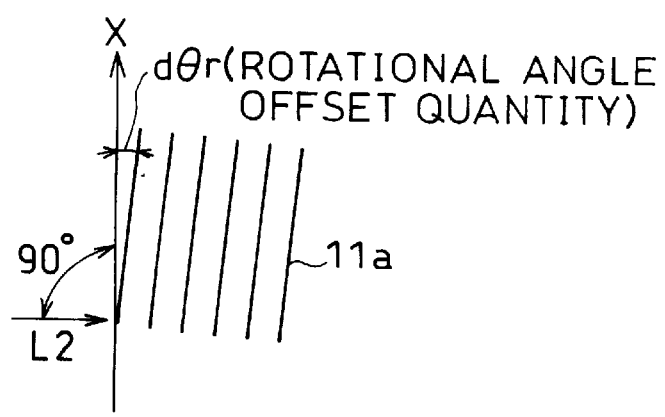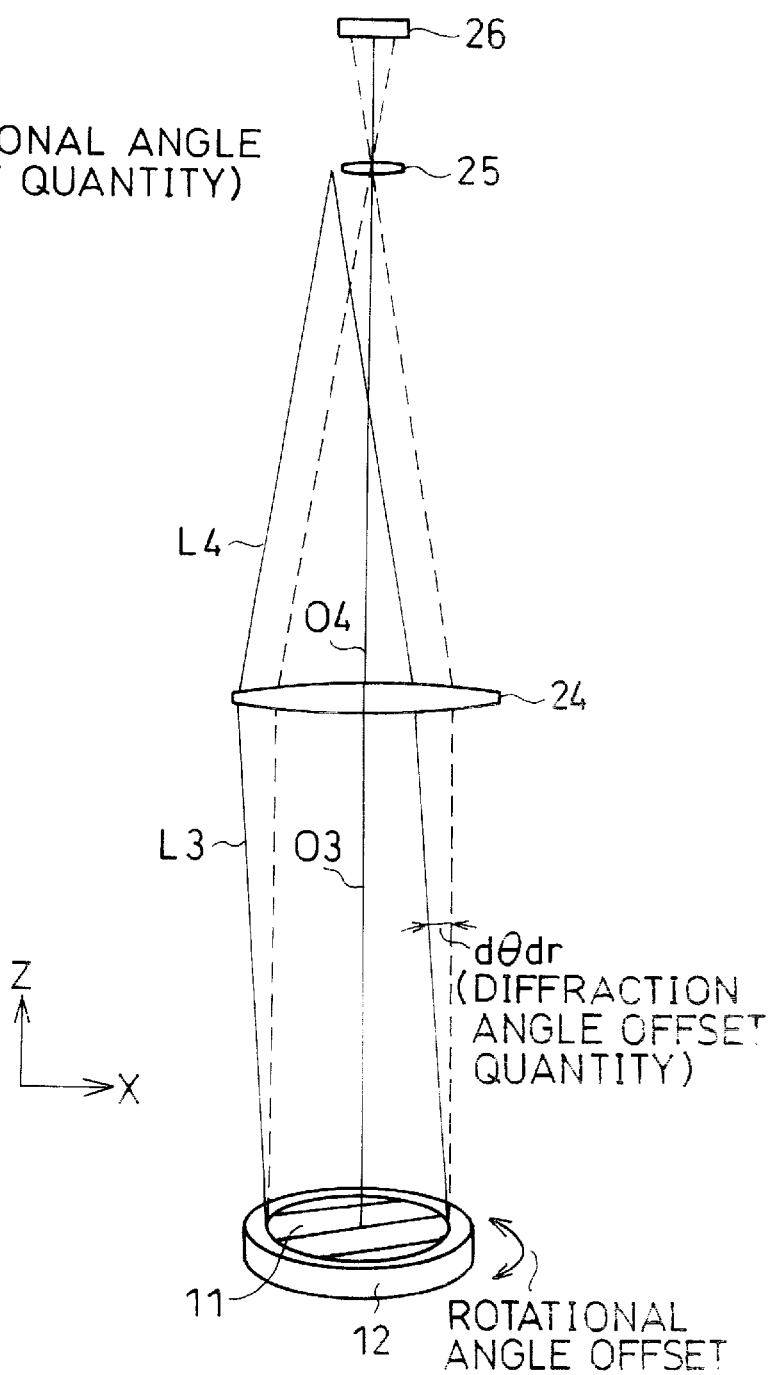

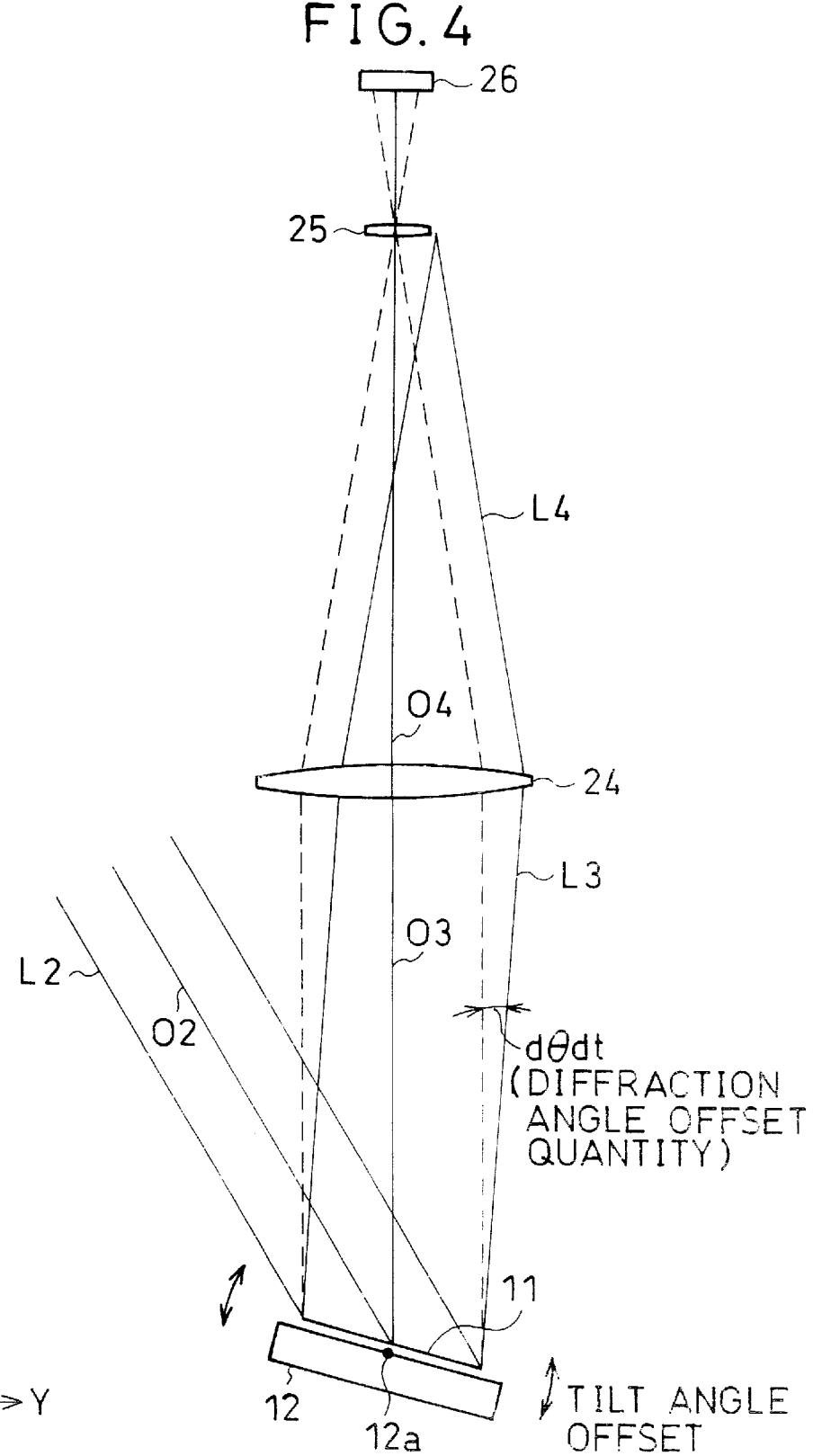

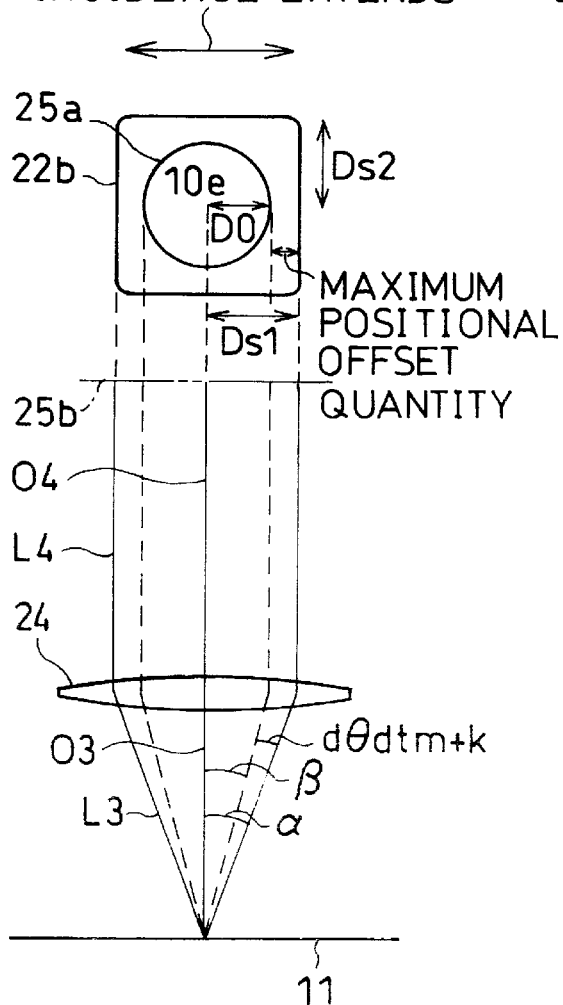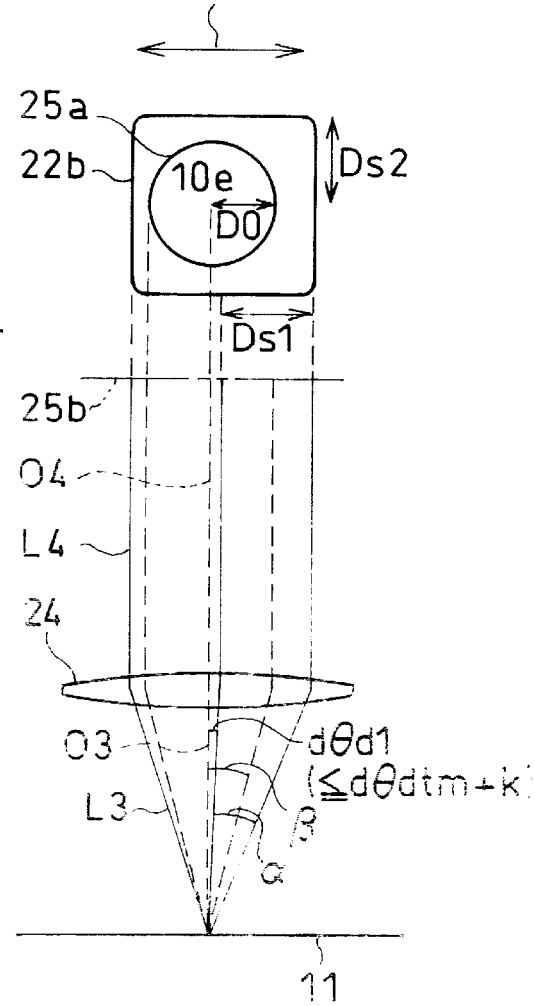

30 DEFECT INSPECTION APPARATUS
13 ILLUMINATION OPTICAL SYSTEM
14 LIGHT-RECEIVING OPTICAL SYSTEM

SCANNING DIRECTION

SCANNING DIRECTION

31b SECONDARY LIGHT SOURCE
DIRECTION ALONG WHICH PLANE OF INCIDENCE EXTENDS

DEFECT INSPECTION APPARATUS

INCORPORATION BY REFERENCE

The disclosure of the following priority application is herein incorporated by reference:

Japanese Patent Application No. 2000-36396 filed Feb. 15, 2000

BACKGROUND OF THE INVENTION

1. Field of the Invention

The present invention relates to a defect inspection apparatus that inspects defects on a substrate and, in particular, a defect inspection apparatus that inspects for irregularities, scars and the like on a substrate.

2. Related Art

There are apparatuses proposed in the prior art that perform automatic inspection for defects such as irregularities, scars and the like at a surface of an IC wafer or a liquid crystal substrate (hereafter generically referred to as a "substrate") by using diffracted light originating from a repetitive pattern formed at the surface.

Since the diffraction efficiency at a position where a defect is present differs from diffraction efficiency at a defect-free position at the substrate surface, a difference in brightness manifests in an image formed from the diffracted light from the repetitive pattern, thereby enabling identification of the position of a defect based upon the contrast in the image.

At the position of a defect, for instance, the cross sectional shape of the repetitive pattern may have been changed due to defocusing of the exposure apparatus or a change may have occurred in the film thickness of the resist.

As illustrated in the side elevation in FIG. 12(a), a substrate 101 to undergo inspection is placed on a stage 102 and is illuminated by parallel illuminating light L11 for inspection. At this time, the illuminating light L11 enters the substrate at a 90° angle relative to the direction along which the straight lines in a repetitive pattern 101a extend (direction X) on the substrate 101 as shown in the top view presented in FIG. 12(b).

Diffracted light L12 (see FIG. 12(a)) from the substrate 101 illuminated with the illuminating light L11 is generated at a given position in the repetitive pattern 101a at a degree of diffraction efficiency that reflects whether a defect is present in the area or the area is free of defect.

In such an apparatus, in which a light-receiving optical system that receives the diffracted light L12 is normally fixed, the diffracted light L12 is guided to the light-receiving optical system by tilting the stage 102 around the axis extending along direction X. The angle setting (tilt angle) at which the stage 102 is tilted is determined in advance in conformance to the diffraction conditions.

The ideal diffraction conditions may be expressed as in the following expression (11) in which λ and θi respectively represent the wavelength and the angle of incidence of the illuminating light L11, θd and m respectively represent the angle of diffraction and the diffraction order of the diffracted light L12, θt represents the tilt angle of the stage 102 and p represents the pitch of the repetitive pattern 101a.

(mathematical expression 1)

$$\sin(\theta d - \theta t) - \sin(\theta i + \theta t) = \frac{m\lambda}{p} \quad (11)$$

In expression (11), the angle of incidence θi, the angle of diffraction θd and the tilt angle θt are set in reference to the standard normal line (reference normal line) achieved when the substrate 101 is held in a level state, as illustrated in FIG. 13. The angle of incidence θi is positive along the direction looking toward the incidence side and is negative along the direction looking toward the reflection side. The range of the angle of incidence θi is 0°<θi<90°.

The angle of deflection θd and the tilt angle θt are both negative along the direction looking toward the incidence side and are positive along the direction looking toward the reflection side. The diffraction order m is negative along the direction looking toward the incidence side and is positive along the direction looking toward the reflection side relative to 0-order diffracted light (regular reflected light) at m=0.

However, there are limits to the degree of accuracy at which the substrate 101 can be positioned along the direction of the tilt angle θt and the degree of accuracy at which the direction of the straight lines of the repetitive pattern 101a on the substrate 101 can be positioned at a 90° angle relative to the direction along which the illuminating light L11 is irradiated for illumination and, thus, there is a problem in that an angular misalignment occurs between the direction along which the diffracted light L12 originating from the repetitive pattern 101a advances (the angle within the YZ plane, i.e., the angle of diffraction θd and the angle within the XZ plane in FIG. 12) and the direction along which the optical axis of the light-receiving optical system extends.

In addition, such an angular misalignment also occurs to a degree corresponding to the extent of an aberration present at an illumination optical system that guides the illuminating light L11 to the substrate 101 or the light-receiving optical system that receives the diffracted light L12. There is an added problem concerning the angular misalignment attributable to an aberration in that the quantity of misalignment varies depending upon the position at which the diffracted light L12 is generated (the position on the substrate 101).

Such an angular misalignment may result in some of the diffracted light L12 advancing outside the pupil of the light-receiving optical system, which will lower the overall contrast or partially lower the contrast of the image formed from the diffracted light L12 to compromise the reliability of the inspection.

SUMMARY OF THE INVENTION

An object of the present invention is to provide a defect inspection apparatus that achieves highly reliable inspection results by preventing the contrast of the image of the substrate formed from the diffracted light from becoming lowered either in its entirety or in part even when there is an angular misalignment between the direction along which the diffracted light from the substrate advances and the direction of the optical axis of the light-receiving optical system.

In the defect inspection apparatus according to the present invention having an illumination optical system that illuminates a substrate and a light-receiving optical system that receives diffracted light from the substrate to inspect for a defect at the substrate based upon an image of the substrate obtained by the light-receiving optical system, the illumination optical system and the light-receiving optical system have numerical apertures different from each other and the absolute value of the difference between the numerical aperture at the illumination optical system and the light-receiving optical system is set at a value equal to or greater than the degree of the angular misalignment manifesting between the direction along which the diffracted light advances and the direction along which the optical axis of the light-receiving optical system extends.

Thus, even when there is an angular misalignment manifesting between the direction along which the diffracted light advances and the direction along which the optical axis of the light-receiving optical system extends, the quantity of diffracted light passing through the pupil of the light-receiving optical system is sustained at a constant level. As a result, the contrast of the image of the substrate formed from the diffracted light having passed through the pupil of the light-receiving optical system is not lowered, either in its entirety or in part. In other words, the image of the substrate has a contrast that reflects whether or not a defect is present. Consequently, the presence/absence of a defect at the substrate can be inspected based upon the image of the substrate thus obtained.

The absolute value of the difference between numerical apertures is set at a value equal to or greater than the angular offset quantity attributable to a rotational angle offset of the substrate relative to a normal line of the substrate along a direction perpendicular to a plane of incidence containing the optical axis of the illumination optical system and the normal line of the substrate.

The absolute value of the difference between numerical apertures is set at a value equal to or greater than the angular offset quantity attributable to a rotational angle offset of the substrate relative to an axis perpendicular to a plane of incidence containing the optical axis of the illumination optical system and a normal line of the substrate along a direction parallel to the plane of incidence.

Both the illumination optical system and the light-receiving optical system or either the illumination optical system or the light-receiving optical system includes at least one reflection optical system and the absolute value of the difference between numerical apertures is set at a value equal to or greater than the angular offset quantity attributable to an aberration at the reflection optical system, along a direction parallel to an off-axis plane of the reflection optical system.

Angular offset quantity k attributable to the aberration is expressed as in expression (1) when an off-axis angle ø (rad) and a focal length $f$ (mm) of the reflection optical system and a radius R (mm) of the substrate satisfy conditions expressed as $-R/f < -0.3438\emptyset - 0.0025$;

$$k = k1(R/f)^3 + k2(R/f)^2 + k3(R/f) + k4 \quad (1),$$

is expressed as in expression (2) when conditions expressed as $-R/f \geq -0.3438\emptyset - 0.0025$ are satisfied;

$$k = 2(k1(R/f)^3 + k3(R/f)) \quad (2);$$

and coefficients k1, k2, k3 and k4 in expressions (1) and (2) expressing the angular offset quantity k are expressed as in expressions (3), (4), (5) and (6) respectively;

$$k1 = 0.8942\emptyset^2 - 0.0317\emptyset + 0.1312 \quad (3)$$

$$k2 = 0.4611\emptyset^2 + 0.7738\emptyset \quad (4)$$

$$k3 = 0.5768\phi^2 - 0.0075\phi + 0.0007 \quad (5)$$

$$k4 = 0.0903\phi^3$$

The numerical aperture at the illumination optical system is larger than the numerical aperture at the light-receiving optical system and the illumination optical system is provided with a means for scanning that scans a surface set at a position conjugate with a pupil of the illumination optical system at least along a linear direction.

BRIEF DESCRIPTION OF THE DRAWINGS

FIG. 3 illustrates a diffraction angle offset attributable to a rotational angle offset of the wafer 11;

FIG. 4 illustrates a diffraction angle offset attributable to a tilt angular offset of the wafer 11;

FIG. 7 illustrates a light flux that is allowed to pass through the pupil of the light-receiving optical system 14;

DETAILED DESCRIPTION OF THE PREFERRED EMBODIMENTS

The following is a detailed explanation of embodiments of the present invention, given in reference to the drawings.

First Embodiment

Figure 1:
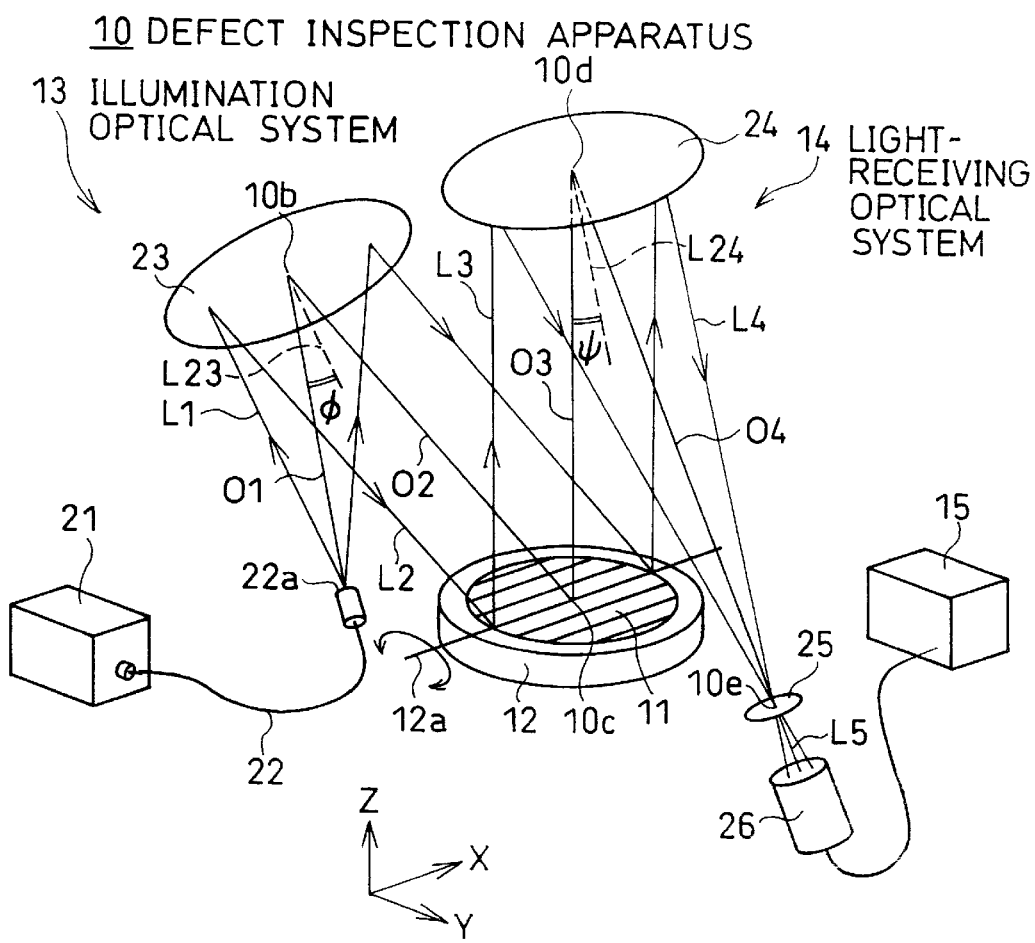
FIG. 1 illustrates the overall structure of the defect inspection apparatus 10 in the first embodiment.

As shown in FIG. 1, a defect inspection apparatus 10 in the first embodiment comprises an inspection stage 12 upon which a wafer 11 is placed, an illumination optical system 13 that illuminates the wafer 11 placed on the inspection stage 12, a light-receiving optical system 14 that receives diffracted light from the wafer 11 illuminated by the illumination optical system 13 and an image processing device 15 that detects the presence/absence of a defect based upon an image of the wafer 11 obtained through the light-receiving optical system 14.

A tilt mechanism (not shown) is provided at the inspection stage 12. The inspection stage 12 is capable of tilting around a tilt axis 12a within a specific angular range.

In the explanation direction X represents the direction extending parallel to the tilt axis 12a of the inspection stage 12. Direction Z represents the direction extending parallel to the normal line (reference normal line) achieved when the inspection stage 12 (the wafer 11) is held in a level state. Direction Y extends perpendicular to direction X and direction Z.

The illumination optical system 13 of the defect inspection apparatus 10 comprises a lamp housing 21, a light guide 22 and a concave reflecting mirror 23.

Figure 13:
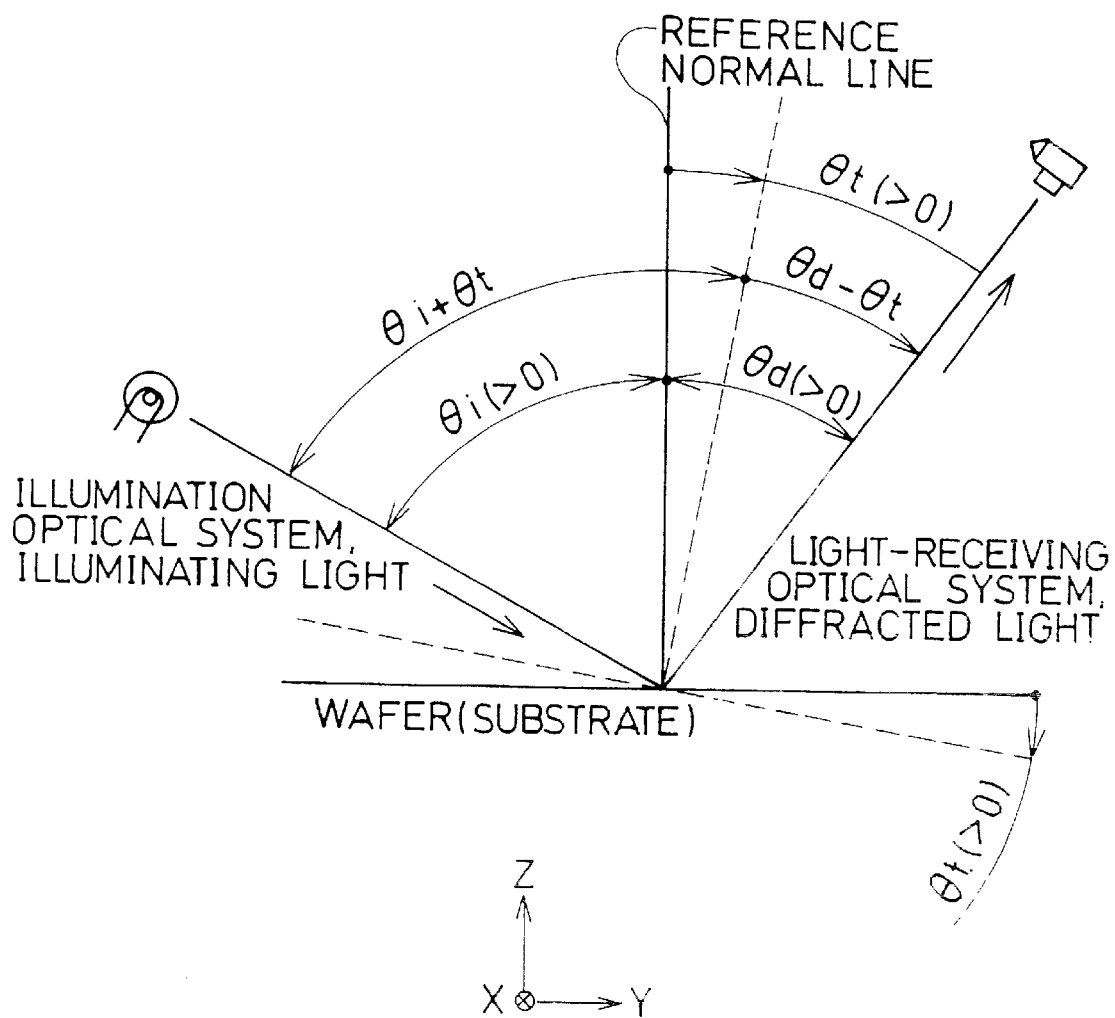
FIG. 13 illustrates parameters in diffraction conditions.

The concave reflecting mirror 23 is a reflecting mirror having a reflecting surface constituted of the inside of a spherical surface and is provided diagonally above the inspection stage 12. In more specific terms, it is positioned so that an axis (an optical axis O2) passing through a center 10b of the concave reflecting mirror 23 and a center 10c of the inspection stage 12 extends parallel to the YZ plane and that the optical axis O2 is inclined at a specific angle (the angle of incidence θi in FIG. 13) relative to direction Z. As a result, the plane (plane of incidence) that contains the optical axis O2 and the normal line of the inspection stage 12 extends parallel to the YZ plane.

The lamp housing 21 is internally provided with a light source such as a halogen lamp or a metal halide lamp, a wavelength selection filter and a lens (none shown). An end surface 22a of the light guide 22 has a roughly rectangular shape (see FIG. 2(a)). The end surface 22a of the light guide 22 constitutes the pupil of the illumination optical system 13.

The light guide 22 (the end surface 22a) and the concave reflecting mirror 23 are positioned so that an axis (an optical axis) O1 passing through their centers 10a and 10b is contained within a plane perpendicular to the plane of incidence (the YZ plane) together with the optical axis O2. The plane that contains the optical axes O1 and O2 and extends perpendicular to the plane of incidence (the YZ plane) as described above is referred to as an "off-axis plane of the concave reflecting mirror 23". It is to be noted that a central axis L23 of the rotation of the concave reflecting mirror 23 and the tilt axis 12a of the inspection stage 12 are both contained within the off-axis plane. In this context, the angle formed by the optical axes O1, O2 and the central axis of rotation L23 is referred to as an "off-axis angle Ø". The illumination optical system 13 is a decentered optical system in which the optical axis O1 and the optical axis O2 do not extend on a single line.

The light guide 22 (the end surface 22a), the concave reflecting mirror 23 and the inspection stage 12 are positioned so that the distance between the centers 10a and 10b and the distance between the centers 10b and 10c are both set equal to the focal length $f$ of the concave reflecting mirror 23 (a telecentric system).

Figure 2A:
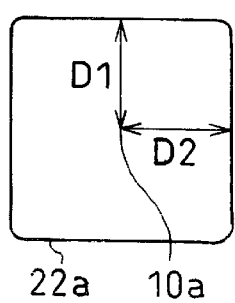
FIG. 2 shows the sizes of the pupil of the illumination optical system 13 and the pupil of 14.

The end surface 22a (rectangular shape) of the light guide 22 is set so that its sides extend parallel to or perpendicular to the plane of incidence (the YZ plane) as shown in FIG. 2(a). D1 indicates the radius of the end surface 22a (the pupil of the illumination optical system 13) along the direction in which the plane of incidence extends and D2 indicates the radius of the end surface 22a along the direction perpendicular to the plane of incidence. The numerical aperture of the illumination optical system 13 on the wafer 11 along the direction parallel to the plane of incidence (a numerical aperture NAi1) is expressed as in expression (12) and the numerical aperture along the direction perpendicular to the plane of incidence (a numerical aperture NAi2) is expressed in expression (13).

$$NAi1 = \frac{D1}{f} \tag{12}$$

$$NAi2 = \frac{D2}{f} \tag{13}$$

In the illumination optical system 13 structured as described above, light within a specific wavelength range λ which is generated by the lamp housing 21 is emitted from the end surface 22a of the light guide 22 toward the concave reflecting mirror 23 (a light flux L1). Since the end surface 22a of the light guide 22 is set on the focal plane of the concave reflecting mirror 23, the light flux L1 from the end surface 22a becomes an almost parallel light flux (illuminating light L2) after having been reflected by the concave reflecting mirror 23 to be irradiated onto the wafer 11 on the inspection stage 12. This illuminating light L2 illuminates the entire surface of the wafer 11.

The light-receiving optical system 14 is constituted of a concave reflecting mirror 24, a lens 25 and an image-capturing element 26. In the light-receiving optical system 14, an aperture 25a (see FIG. 2b) of the lens 25 constitutes the pupil of the light-receiving optical system 14. The aperture 25a of the lens 25 is formed in a round shape. It is to be noted that the position of the aperture 25a of the lens 25 is conjugate with the position of the end surface 22a of the light guide 22.

The concave reflecting mirror 24 at the light-receiving optical system 14 is a reflecting mirror similar to the concave reflecting mirror 23 explained earlier and is set above the inspection stage 12. More specifically, it is positioned so that an axis (an optical axis O3) passing through a center 10d of the concave reflecting mirror 24 and the center 10c of the inspection stage 12 extends parallel to the Z direction (the reference normal line) and is also contained within the plane of incidence.

The concave reflecting mirror 24 and the lens 25 (the aperture 25a) are positioned so that an axis (the optical axis O4) passing through their centers 10d and 10e is contained within the plane of incidence together with the optical axis O3. Thus, the plane containing the optical axes O3 and O4 (the off-axis plane of the concave reflecting mirror 24) is aligned with the plane of incidence.

It is to be noted that this off-axis plane also contains a central axis L24 of the rotation of the concave reflecting mirror 24. In this context, the angle formed by the optical axes O3, O4 and the central axis of rotation L24 is referred to as an "off-axis angles". The light-receiving optical system 14 is a decentered optical system in which the optical axis O3 and the optical axis O4 do not extend along a single line.

In addition, the inspection stage 12, the concave reflecting mirror 24 and the lens 25 (the aperture 25a) are positioned so that the distance between the centers 10c and 10d and the distance between the centers 10d and 10e are both set equal to the focal length $f$ of the concave reflecting mirror 24 (telecentric system). It is to be noted that the focal length $f$ of the concave reflecting mirror 24 is equal to the focal length $f$ of the concave reflecting mirror 23.

The numerical aperture of the light-receiving optical system 14 on the wafer 11 is expressed as in following expression (14), assuming that the numerical aperture (a numerical aperture NAo1) along the direction parallel to the plane of incidence and the numerical aperture (a numerical aperture NAo2) along the direction perpendicular to the plane of incidence are equal to each other and that Do represents the radius of the aperture 25a (the pupil of the light-receiving optical system 14) of the lens 25.

$$NAo1 = NAo2 = \frac{Do}{f} \quad (14)$$

In the light-receiving optical system 14 structured as described above, diffracted light L3 from the wafer 11 is first reflected at the concave reflecting mirror 24 and becomes a converging light flux L4 which then reaches the aperture 25a (the pupil of the light-receiving optical system 14) of the lens 25. Diffracted light L5 having passed through the aperture 25a (the pupil of the light-receiving optical system 14) of the lens 25 is then condensed onto the image-capturing surface of the image-capturing element 26. On the image-capturing surface of the image-capturing element 26, an image of the wafer 11 is formed by the diffracted light L5.

It is to be noted that the radius Do of the aperture 25a of the lens 25 is set in correspondence to the focal depth required at the surface of the wafer 11. Since the surface of the wafer 11 moves along direction Z when the inspection stage 12 is tilted within the specific angular range, a focal depth that contains this range of movement must be achieved.

The image processing device 15 connected to the image-capturing element 26 monitors the quantity of light at the image in addition to performing image processing on the image taken in at the image-capturing element 26. The image processing device 15 also extracts characteristics of the pattern at the wafer 11 undergoing the inspection and engages in pattern matching of the pattern with the image of a good wafer stored in advance to make a decision as to whether or not there is a portion in the pattern that differs from the characteristics of the image of the good wafer. If there is any inconsistency in the contrast of the diffracted image, the inconsistent area is output as a defect based upon the difference in the contrast or the characteristics manifesting in the area.

In the defect inspection apparatus 10 in the embodiment, the numerical apertures at the illumination optical system 13 are different from the numerical apertures at the light-receiving optical system 14, with the numerical apertures NAi1 and NAi2 (see expressions (12) and (13)) at the illumination optical system 13 set larger than the numerical apertures NAo1 and NAo2 (see expression (14)) at the light-receiving optical system 14.

The differences between the numerical apertures at the illumination optical system 13 and at the light-receiving optical system 14 (NAi1−NAo1, NA i2−NA o2) are set in correspondence to the degree of the angular misalignment between the direction along which the diffracted light L3 from the wafer 11 advances and the optical axis O3 of the light-receiving optical system 14.

Since the optical axis O3 of the light-receiving optical system 14 is fixed in the defect inspection apparatus 10, the degree of the angular misalignment mentioned above may be considered as the degree by which the diffracted light L3 is offset along the advancing direction. Hereafter, the degree to which the diffracted light L3 is offset along the advancing direction is referred to as a "diffraction angle offset quantity dθd".

Next, the diffraction angle offset quantity dθd manifesting in the defect inspection apparatus 10 structured as described above is examined.

There are three conceivable causes that may result in a diffraction angle offset. The first cause is angular offset occurring in the rotation of the wafer 11 around the normal line. The second cause is an angular offset in the rotation of the wafer 11 around the tilt axis 12a. The third cause is an aberration at the concave reflecting mirror 23 or 24. These three causes are now individually examined.

(1) A diffraction angle offset resulting from an angular offset in the rotation of the wafer 11 around the normal line is examined.

Under normal circumstances, the rotational angle of the wafer 11 to undergo the inspection at which it rotates around the normal line is adjusted through an alignment implemented on an external alignment stage (not shown) so that the direction along which the straight lines of the repetitive pattern at the wafer 11 extends set parallel to direction X (perpendicular to the optical axis O2) before the wafer 11 is placed on the inspection stage 12. When the alignment is completed, the wafer 11 is set on the inspection stage 12 while maintaining the rotational angle achieved through the adjustment.

However, while replacing the wafer 11 onto the inspection stage 12, the wafer 11 may be caused to rotate slightly around the normal line due to a mechanical error. If the wafer 11 rotates even by a small degree around the normal line, the direction along which the straight lines of the repetitive pattern 11a extend becomes offset from direction X (rotational angle offset quantity dθr), as shown in FIG. 3(a).

In addition, the alignment is performed by using an external reference on the premise that the direction along which the straight lines of the repetitive pattern 11a extend is either parallel to or perpendicular to the external reference (such as an orientation flat or notch) at the wafer 11. However, the coordinate system set in conformance to the external reference and the coordinate system of an exposed shot may be offset from each other around the normal line of the wafer 11 due to an error of the exposure apparatus or the like. In such a case, the rotational angle offset quantity dθr shown in FIG. 3(a) further increases.

If the wafer 11 manifests a rotational angle offset around the normal line (at a rotational angle offset quantity dθr) and the direction along which the straight lines of the repetitive pattern 11a extend is offset from direction X in this manner, the direction in which the illuminating light L2 is irradiated becomes offset from the direction extending perpendicular to the direction along which the straight lines of the repetitive pattern 11a extend.

As a result, the direction along which the diffracted light L3 originating from the repetitive pattern 11a of the wafer 11 advances becomes offset from the optical axis O3 of the light-receiving optical system 14 (at a diffraction angle offset quantity dθdr) within a plane (the XZ plane) that is perpendicular to the plane of incidence and contains the optical axis O3, as indicated by the solid line in FIG. 3(b). It is to be noted that in order to simplify the illustration, the concave reflecting mirror 24 is shown as a convex lens in FIG. 3(b).

The relationship between the rotational angle offset quantity dθr and the diffraction angle offset quantity dθdr may be expressed as in the following approximate expression (15) as disclosed in Japanese Laid-Open Patent Publication No. 11-6803, as long as dθr and dθdr represent very small values. In the expression, m represents the diffraction order of the diffracted light L3, λ represents the wavelength of the illuminating light L11 and p represents the pitch of the repetitive pattern 11a. The units of dθr and dθdr are radians.

$$d\theta dr = \left|\left(\frac{m\lambda}{p}\right)d\theta r\right| \quad (15)$$

By converting the expression (11) to the form of a product in order to facilitate the examination of the maximum value (dθdrm) of the diffraction angle offset quantity dθdr in the defect inspection apparatus 10 in the embodiment, the following expression (16) is obtained.

$$2\cos\left(\frac{\theta d + \theta i}{2}\right)\sin\left(\frac{\theta d - \theta i}{2} - \theta t\right) = \frac{m\lambda}{p} \quad (16)$$

When in the diffraction order m, the angle of diffraction θd, the angle of incidence θi of the illuminating light L2 and the tilt angle θt in expression (16) respectively assume the following values; m=−1, θd=0°, θi=40° and −20°<(tilt angle θt)<35°, for instance, the following expression (17) is obtained.

$$\left|\frac{\lambda}{p}\right| < 1.54 \quad (17)$$

Thus, based upon expressions (15) and (17), it is ascertained that the maximum value (dθdrm) of the diffraction angle offset quantity dθdr of the diffracted L3 within the XZ plane is approximately 1.54 times the rotational angle offset quantity dθr of the wafer 11.

The rotational angle offset quantity dθr, which represents a quantity obtained by totaling the error occurring when the wafer is placed on the inspection stage 12 and the error of the shot coordinate system relative to the external reference at the wafer 11, can be estimated. Thus, by using an estimated value for the rotational angle offset quantity dθr, the maximum value (dθdrm=1.54 dθr) of the diffraction angle offset quantity of the diffracted light L3 within the XZ plane, too, can be estimated.

For instance, if the rotational angle offset quantity dθr is 0.0015 rad, the maximum value (dθdrm) of the diffraction angle offset quantity dθdr is 0.0023 rad.

(2) Now, a diffraction angle offset manifesting as a result of a rotational angle offset of the wafer 11 around the tilt axis 12a is examined.

The inspection stage 12 (the wafer 11) is tilted to guide the diffracted light L3 at a desired diffraction order m originating from the wafer 11 to the light-receiving optical system 14. However, the inspection stage 12 may be tilted at an angle slightly deviated from the tilt angle θt that has been set due to a mechanical error.

If the wafer 11 manifests a rotational angle offset (at a tilt angle offset quantity dθt) around the tilt axis 12a as described above, the direction along which the diffracted light L3 originating from the wafer 11 advances (at an angle of diffraction θd) becomes offset from the optical axis O3 of the light-receiving optical system 14 within the plane of incidence (parallel to the YZ plane), as indicated by the solid line in FIG. 4. It is to be noted that in FIG. 4, too, the concave reflecting mirror 24 is shown as a convex lens in order to simplify the illustration.

By calculating the total differential of expression (11) representing the diffraction conditions described above in order to investigate the relationship between the tilt angle offset quantity dθt and the diffraction angle offset quantity dθdt manifesting at this time, expression (18) is obtained.

$$\frac{m}{p}d\lambda = d\theta dt \cos(\theta d - \theta t) - d\theta i \cos(\theta i + \theta t) - \quad (18)$$
$$d\theta t\{\cos(\theta d - \theta t) + \cos(\theta i + \theta t)\}$$

In order to simplify the explanation, it is assumed that the illuminating light L2 is a monochromatic light (dλ=0) and that there is no error with regard to the angle of incidence θi (dθi=0). In addition, since the optical axis O3 of the light-receiving optical system 14 is parallel to the direction Z (the reference normal line), the angle of diffraction θd of the diffracted light L3 is; θd=0. Under these circumstances, the following expression (19) is obtained from expression (18) above.

$$d\theta dt = d\theta t\left\{1 + \frac{\cos(\theta i + \theta t)}{\cos \theta t}\right\} \quad (19)$$

If the angle of incidence θi of the illuminating light L2 and the tilt angle θt in expression (19) respectively assume the following values; θi=40° and −20°<(tilt angle θt)<35° in order to facilitate the examination of the maximum value (dθdtm) of the diffraction angle offset quantity dθdt in the defect inspection apparatus 10 in the embodiment, the diffraction angle offset quantity dθdt changes over a range in which it is 1.32~2.0 times the tilt angle offset quantity dθt.

Thus, the maximum value (dθdtm) of the diffraction angle offset quantity dθdt of the diffracted light L3 within the plane of incidence is approximately twice the tilt angle offset quantity dθt of the wafer 11. It is to be noted that the tilt angle θt at which the diffraction angle offset quantity dθdt achieves the maximum value (dθdtm) is −20° within the range set above.

Since the tilt angle offset quantity dθt can be estimated, the maximum value (dθdtm=2.0 dθt) of the diffraction angle offset quantity dθdt of the diffracted light L3 within the plane of incidence can be estimated by using the estimated value of the tilt angle offset quantity dθt.

For instance, when the tilt angle offset quantity dθt is 0.001 rad, the maximum value (dθdtm) of the diffraction angle offset quantity dθdt is 0.002 rad.

(3) A diffraction angle offset manifesting as a result of an aberration at the concave reflecting mirror 23 or 24 is now examined. A diffraction angle offset attributable to an aberration at the concave reflecting mirror 23 of the illumination optical system 13 is discussed as an example.

As explained earlier, since the illumination optical system 13 is a decentered optical system in which the optical axis O1 and the optical axis O2 do not extend on a single line, the direction along which the illuminating light L2 advances becomes offset by a very small degree (an incidence angular offset quantity dθi) from the optical axis O2 within the off-axis plane (plane perpendicular to the plane of incidence) of the concave reflecting mirror 23 due to an aberration at the concave reflecting mirror 23.

If the direction along which the illuminating light L2 advances becomes offset from the optical axis O2 in this manner, the direction along which the diffracted light L3 from the wafer 11 advances, too, becomes offset from the optical axis O3 of the light-receiving optical system 14 (by a diffraction angle offset quantity dθdi). Since the illuminating light L2 becomes offset within a plane (the off-axis plane) perpendicular to the plane of incidence, diffracted light L3, too, becomes offset within a plane (the XZ plane containing the optical axis O3) perpendicular to the plane of incidence.

Since the resulting diffraction angle offset quantity dθdi is equal to the incidence angular offset quantity dθi of the illuminating light L2, the incidence angular offset quantity dθi is now examined.

Table 1 presents the simulation results with regard to the incidence angular offset quantity dθi measured by setting the off-axis angle ø of the concave reflecting mirror 23 at 10°.

TABLE 1

| POINT REACHED ON WAFER Xp (MM) | INCIDENCE ANGULAR OFFSET QUANTITY dθi (rad) |
|---|---|
| −0.5f | −0.0094 |
| −0.4f | −0.0068 |
| −0.3f | −0.0039 |
| −0.2f | −0.0012 |
| −0.1f | −0.0003 |
| 0 | 0 |
| 0.1f | −0.0031 |
| 0.2f | −0.0100 |
| 0.3f | −0.0217 |
| 0.4f | −0.0395 |
| 0.5f | −0.0643 | f: FOCAL LENGTH (mm)

As the results presented in Table 1 indicate, the incidence angular offset quantity dθi changes in correspondence to the point (X position) Xp (mm) at which the illuminating light L2 reaches the wafer 11. The reach point Xp on the wafer 11 represents the distance Xp (mm) from the center 10c of the wafer 11 (see FIG. 5). The simulation was conducted within a range of $|Xp| \leq 0.5f$.

Figure 5:
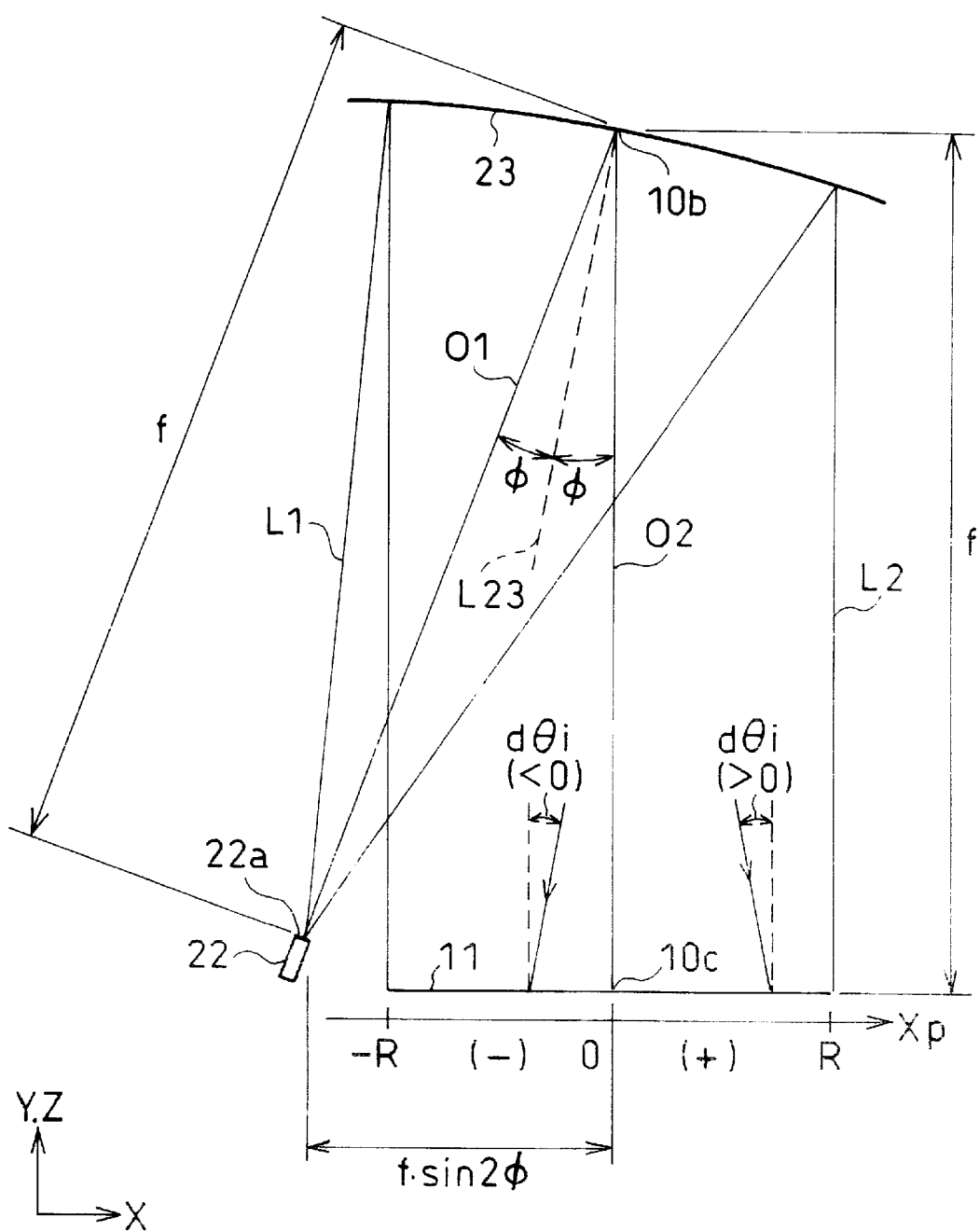
FIG. 5 illustrates an incidence angular offset attributable to an aberration at the concave reflecting mirror 23.
Figure 6:
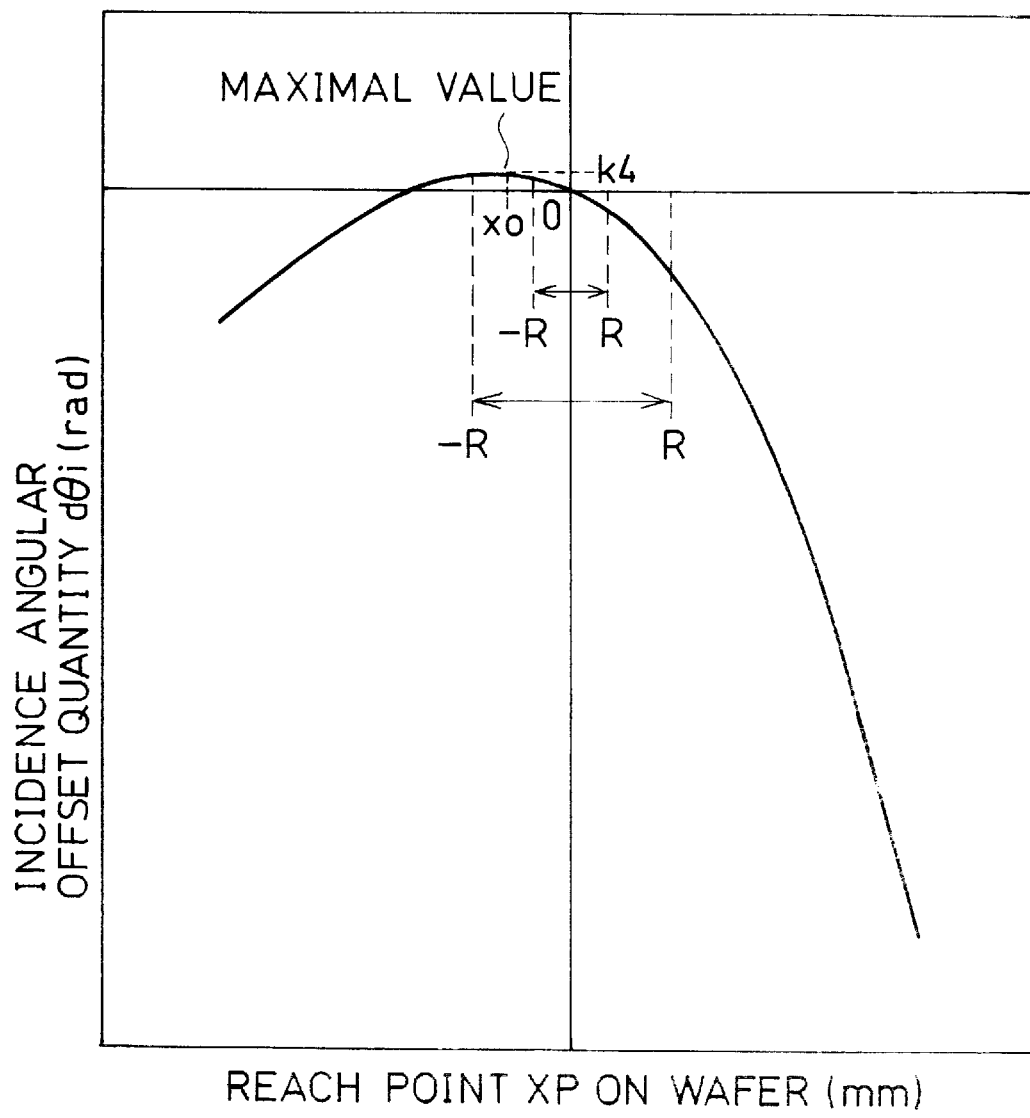
FIG. 6 illustrates a graph of the incidence angular offset quantity dθi attributable to the aberration at the concave reflecting mirror 23.

It is to be noted that as shown in FIG. 5, the incidence angular offset quantity dθi is positive along the counter-clockwise direction and negative along the clockwise direction in the sheet of paper on which FIG. 5 is drawn. In addition, the reach point Xp at which the illuminating light reaches the wafer 11 is positive toward the right and is negative toward the left of the sheet of paper. The concave reflecting mirror 23 is set off axis along the direction in which the light guide 22 is set toward the negative side of Xp.

In Table 1, the maximum value (dθia) of the incidence angular offset quantity dθi of the illuminating light L2 is 0.0003 rad corresponding to a reach point Xp at −0.1f on the wafer 11. The minimum value (dθib) is −0.0643 rad corresponding to a reach point Xp at 0.5f. In addition, the angular width between the maximum value (dθia) and the minimum value (dθib) of the incidence angular offset quantity dθi is 0.0646 rad.

A simulation was also conducted with regard to the incidence angular offset quantity dθi by setting the off-axis angle ø of the concave reflecting mirror 23 at angles other than 10°. It is to be noted that experience in optical design indicates that the off-axis angle ø of the concave reflecting mirror 23 should be equal to or smaller than 15°, and that it is desirable that $R/f < \sin 2ø$ should be satisfied in order to ensure that the wafer 11 and the light guide 22 do not interfere with each other. The simulation was implemented within this range of the off-axis angle ø.

The simulation results obtained at varying off-axis angles ø indicate that the maximal value of the incidence angular offset quantity dθi is invariably achieved on the negative side of the reach point Xp on the wafer 11, that the incidence angular offset quantity dθi is at 0 at the center 10c of the wafer 11 (reach point Xp=0) and that the value becomes steadily reduced on the positive side of the reach point Xp.

Now, the incidence angular offset quantity dθi is approximated in a cubic expression (expression (21)) of the reach point Xp on the wafer 11, by ensuring that the simulation results obtained at the varying off-axis angles ø are satisfied.

$$d\theta i = -k1(Xp/f)^3 - k2(Xp/f)^2 - k3(Xp/f) \quad (21)$$

In addition, individual coefficients k1, k2 and k3 in expression (21) are expressed as functions of the off-axis angle ø (expressions (22), (23) and (24)). It is to be noted that the unit of the off-axis angle ø is radians.

$$k1 = 0.8942\varphi^2 - 0.0317\varphi + 0.1312 \quad (22)$$

$$k2 = 0.4611\varphi^2 + 0.7738\varphi \quad (23)$$

$$k3 = 0.5768\varphi^2 - 0.0075\varphi + 0.0007 \quad (24)$$

The reach point Xo at which the incidence angular offset quantity dθi achieves the maximal value (extreme value) and the corresponding incidence angular offset quantity k4 are respectively expressed through the following expressions (25) and (26).

$$Xo/f = -0.3438\varphi - 0.0025 \quad (25)$$

$$k4 = 0.0903\varphi^3 \quad (26)$$

Since the distance between the center 10c (Xp=0) of the wafer 11 to the outermost circumference on the positive side is equal to the distance between the center 10c and the outermost circumference on the negative side, the reach point Xp that determines the minimum value (dθib) of the incidence angular offset quantity dθi is always at the outermost circumference on the positive side. The minimum value (dθib) of the incidence angular offset quantity dθi is expressed as in the following expression (27) by substituting Xp with R (Xp=R) in expression (21).

$$d\theta ib = -k1(R/f)^3 - k2(R/f)^2 - k3(R/f) \quad (27)$$

The maximum value (dθia) of the incidence angular offset quantity dθi is on the negative side of the reach point Xp. If the maximal value k4 (see expression (26)) of the incidence angular offset quantity dθi is within the range between the center 10c (Xp=0) of the wafer 11 and the outermost circumference (Xp=−R) on the negative side (−R<Xo), the maximal value k4 is the maximum value (dθia) of the incidence angular offset quantity dθi. In this case, the angular width k between the maximum value (dθia) and the minimum value (dθib) of the incidence angular offset quantity dθi is expressed through the following expression (28) based upon expressions (26) and (27).

$$k = d\theta ia + |d\theta ib| = k1(R/f)^3 + k2(R/f)^2 + k3(R/f) + k4 \quad (28)$$

(with −R/f<−0.3438ø−0.0025)

If, on the other hand, the maximal value k4 (see expression (26)) of the incidence angular offset quantity dθi is not within the range between the center 10c (Xp=0) of the wafer 11 and the outermost circumference (Xp=−R) on the negative side (−R≧Xo), the incidence angular offset quantity dθi at the outermost circumference (Xp=−R) on the negative side achieves the maximum value (dθia). The maximum value (dθia) in this case is expressed through the following expression (29) by substituting Xp with −R (Xp=−R) in expression (21).

$$d\theta ia = k1(R/f)^3 - k2(R/f)^2 + k3(R/f) \quad (29)$$

The angular width k between the maximum value (dθia) and the minimum value (dθib) of the incidence angle offset quantity dθi under these circumstances is expressed through the following expression (31) based upon expressions (27) and (29).

$$k = d\theta ia + |d\theta ib| = 2(k1(R/f)^3 + k3(R/f)) \quad (31)$$

(with $-R/f \geq 0.3438\emptyset - 0.0025$)

Since the incidence angular offset quantity dθi of the illuminating light L2 attributable to the aberration at the concave reflecting mirror 23 has the angular width k (see expression (28) or (31)) as explained above, the diffraction angle offset quantity dθdi of the diffracted light L3 from the wafer 11, too, has the same angular width k.

For instance, when the off-axis angle ø is 10° (0.174 rad), the radius R of the wafer 11 is 100 mm and the focal length f of the concave reflecting mirror 23 is 600 mm, the angular width k of the incidence angular offset quantity dθi (the diffraction angle offset quantity dθdi) is 0.0082 rad calculated through expression (28). It is to be noted that the individual coefficients are set at; k1=0.1529, k2=0.1491, k3=0.0170 and k4=0.00048.

The logic discussed above can be directly applied to the concave reflecting mirror 24 at the light-receiving optical system 14 as well. In the case of the concave reflecting mirror 24, in which the off-axis plane of the concave reflecting mirror 24 is aligned with the plane of incidence, the illuminating light L2 is offset from the optical axis O2 and the diffracted light L3 is offset from the optical axis O3 within the plane of incidence. Namely, the offset directions differ from those at the concave reflecting mirror 23 since the off-axis plane is set differently. However, as long as the off-axis angle ψ is the same, the angular width k of the incidence angular offset quantity dθi (the diffraction angle offset quantity dθdi) does not change (see expression (28) or (31)).

As is clear from the discussion above, at the defect inspection apparatus 10 in the embodiment, a diffraction angle offset occurs in the direction that is horizontal relative to the plane of incidence (the YZ plane) due to a tilt angle offset (see FIG. 4) of the wafer 11 and an aberration of the concave reflecting mirror 24. As a result, the diffraction angle offset quantity dθd1 along the direction horizontal to the plane of incidence represents a total of the diffraction angle offset quantity dθdt (see expression (19)) attributable to the tilt angle offset (see FIG. 4) of the wafer 11 and the diffraction angle offset quantity dθdi attributable to the aberration at the concave reflecting mirror 24.

Accordingly, in the defect inspection apparatus 10 in the embodiment, the difference between the numerical aperture NAi1 at the illumination optical system 13 and the numerical aperture NAo1 at the light-receiving optical system 14 along the direction parallel to the plane of incidence (the YZ plane) is set equal to the sum of the maximum value (dθdtm=2.0 dθt) of the diffraction angle offset quantity dθdt and the angular width k (see expression (28) or (31)) of the diffraction angle offset quantity dθdi.

$$Nai1 - NAo1 = d\theta dtm + k \quad (33)$$

Thus, as shown and FIG. 7(a), the radius Ds1 of a spot 22b at a pupil surface 25b (the surface at which the aperture 25a of the lens 25 is set) of the diffracted light L3 originating from a given point on the wafer 11 is expressed as in the following expression (34).

$$Ds1 = \text{(a numerical aperture } NAi1 \text{ at illumination optical system } 13) \times \text{(focal length } f \text{ of the light-receiving optical system } 14) = (NAo1 \cdot f) + ((d\theta dtm + k) \cdot f) \quad (34)$$

In expression (34), the first term (NAo1·f) on the right side represents the radius Do of the pupil (the aperture 25a of the lens 25) of the light-receiving optical system 14 (see expression (14)). In addition, the second term ((dθdtm+k)·f) on the right side can be considered to represent the maximum positional offset quantity of the spot 22b of the diffracted light L3 at the surface 25b of the pupil (the aperture 25a of the lens 25) of the light-receiving optical system 14.

In other words, the radius Ds1 of the spot 22b of the diffracted light L3 at the pupil surface 25b is the sum of the radius Do of the pupil (the aperture 25a of the lens 25) of the light-receiving optical system 14 and the maximum positional offset quantity (dθdtm+k)·f).

Thus, as shown in FIG. 7b, even if there is a diffraction angle misalignment (a tilt angle offset, an aberration at the concave reflecting mirror 24) of the diffracted light L3 from the wafer 11 (diffraction angle offset quantity dθd1≦dθdtm+k) and a positional offset of the diffracted light L3 occurs along the direction in which the plane of incidence extends at the surface 25b of the pupil (the aperture 25a of the lens 25) of the light-receiving optical system 14, the quantity of diffracted light L5 (see FIG. 1) passing through the pupil (the aperture 25a of the lens 25) of the light-receiving optical system 14 remains constant.

A diffraction angle offset along the direction perpendicular to the plane of incidence, on the other hand, occurs due to a rotational angle offset (see FIG. 3) of the wafer 11 and an aberration of the concave reflecting mirror 23. Thus, the diffraction angle offset quantity dθd2 along the direction perpendicular to the plane of incidence is the sum of the diffraction angle offset quantity dθdr (see expression (15)) attributable to the rotational angle offset (see FIG. 3) of the wafer 11 and the diffraction angle offset quantity dθdi attributable to the aberration at the concave reflecting mirror 23.

Accordingly, in the defect inspection apparatus 10 in the embodiment, the difference between the numerical aperture NAi2 at the illumination optical system 13 and the numerical aperture NAo2 at the light-receiving optical system 14 along the direction perpendicular to the plane of incidence (the YZ plane) is set equal to the sum of the maximum value (dθdrm=1.54 dθdr) of the diffraction angle offset quantity dθdr and the angular width k (see expression (28) or (31)) of the diffraction angle offset quantity dθdi, as expressed in expression (34).

$$NAi2 - NAo2 = d\theta drm + k \quad (35)$$

Thus, the radius Ds2 of the spot 22b (see FIG. 7(a)) of the diffracted light L3 from the wafer 11 at the pupil surface 25b is expressed as in the following expression (36).

$$Ds2 = \text{(a numerical aperture } NAi2 \text{ at illumination optical system } 13) \times \text{(focal length } f \text{ of the light-receiving optical system } 14) = NAo2 \cdot f + ((d\theta drm + k) \cdot f \quad (36)$$

In expression (36), the first term (NAo2·f) on the right side represents the radius Do of the pupil (the aperture 25a of the lens 25) of the light-receiving optical system 14 (see expression (14)). In addition, the second term ((dθdrm+k)·f) on the right side can be considered to represent the maximum positional offset quantity of the spot 22b of the diffracted light L3 at the pupil surface 25b.

In other words, the radius Ds2 of the spot 22b of the diffracted light L3 is the sum of the radius Do of the pupil (the aperture 25a of the lens 25) of the light-receiving optical system 14 and the maximum positional offset quantity (dθdrm+k)·f).

Thus, even if there is a diffraction angle misalignment (rotational angle offset, an aberration at the concave reflecting mirror 23) of the diffracted light L3 (diffraction angle offset quantity dθd2≦dθdrm+k) and a positional offset of the diffracted light L3 occurs along the direction perpendicular to the plane of incidence at the pupil surface 25b, the quantity of diffracted light L5 (see FIG. 1) passing through the pupil (the aperture 25a of the lens 25) of the light-receiving optical system 14 remains constant.

It is to be noted that in the defect inspection apparatus 10, in which the focal length f of the concave reflecting mirror 23 of the illumination optical system 13 is equal to the focal length f of the concave reflecting mirror 24 of the light-receiving optical system 14, the differences between the numerical apertures explained above are achieved by assuring a specific difference between the size of the pupil (the end surface 22a of the light guide 22) of the illumination optical system 13 and the size of the pupil (the aperture 25a of the lens 25) of the light-receiving optical system 14. The radius d1 and d2 of the pupil (the end surface 22a of the light guide 22) of the illumination optical system 13 are respectively expressed as in (37) and (38) based upon expressions (12) and (13) and expressions (33) and (35).

$$D1 = NAi1 \cdot f = NAo1 \cdot f + (d\theta dtm + k) \cdot f \qquad (37)$$

$$D2 = NAi2 \cdot f = NAo2 \cdot f + (d\theta dtm + k) \cdot f \qquad (38)$$

As explained above, in the defect inspection apparatus 10 having larger numerical apertures at the illumination optical system 13 than the numerical apertures at the light-receiving optical system 14, the quantity of the diffracted light L5 (see FIG. 1) passing through the pupil (the aperture 25a of the lens 25) of the light-receiving optical system 14 can be sustained at a constant level, even if there is a diffraction angle offset of the L3 from the wafer 11. As a result, the contrast of an image of the wafer 11 formed by the diffracted light L5 is not lowered, either in its entirety or in part. Since the image of the wafer 11 formed by the diffracted light L5 has a contrast reflecting whether or not there is a defect, highly reliable results can be obtained from the defect inspection conducted on the wafer 11.

Since the size of the aperture 25a of the lens 25 at the light-receiving optical system 14 is smaller than the size of the end surface 22a of the light guide 22, a focused detection can be performed at individual points of the wafer 11 even when the focal depth of the light-receiving optical system 14 is large and the wafer 11 is tilted.

It is to be noted that while the quantity of the diffracted light L5 guided to the image-capturing element 26 is reduced as a result of reducing the size of the aperture 25a of the lens 25 at the light-receiving optical system 14, a desired SN ratio can be sustained by raising the detection sensitivity at the image-capturing element 26 and the brightness at the light source inside the lamp housing 21.

While an explanation is given in reference to the first embodiment above on an example in which the numerical apertures at the illumination optical system 13 are set larger than the numerical apertures at the light-receiving optical system 14 (addition), the numerical apertures at the light-receiving optical system 14 may be set larger than the numerical apertures at the illumination optical system 13 instead (subtraction). In this case, too, the quantity of the diffracted light L5 (see FIG. 1) passing through the pupil (the aperture 25a of the lens 25) of the light-receiving optical system 14 can be sustained at a constant level, thereby making it possible to obtain highly reliable results from a defect inspection conducted on the wafer 11.

Second Embodiment

Figure 8:
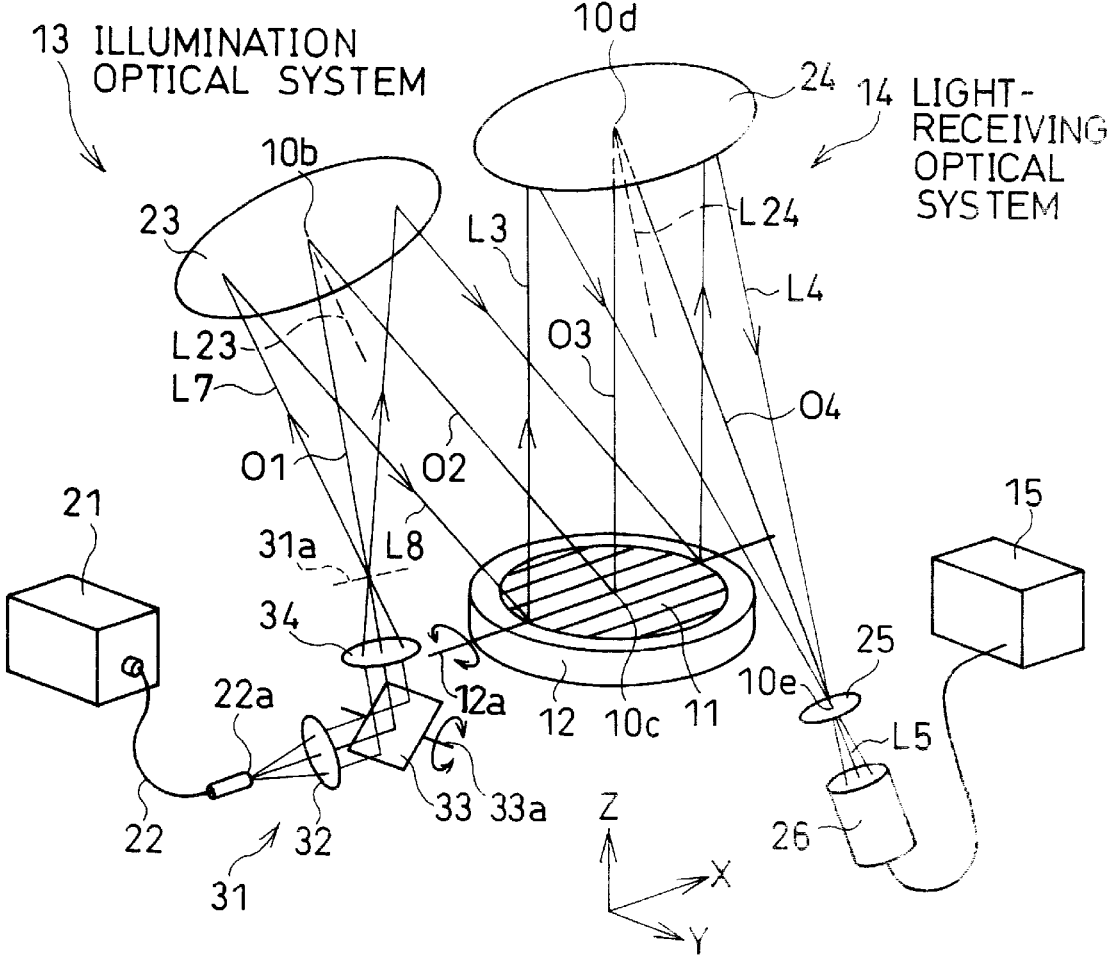
FIG. 8 illustrates the overall structure of the defect detection inspection apparatus 30 in the second embodiment.

As illustrated in FIG. 8, a defect inspection apparatus 30 in the second embodiment is constituted by providing an afocal scanning system 31 (a means for scanning) between the light guide 22 and the concave reflecting mirror 23 of the illumination optical system 13. The end surface 22a of the light guide 22 and a focal plane 31a of the concave reflecting mirror 23 achieve a conjugate relationship via the afocal scanning system 31.

The afocal scanning system 31 comprises a lens 32, an oscillating mirror 33 and a lens 34. The oscillating mirror 33 is capable of rotating around a rotational axis 33a extending parallel to direction Y within a specific deflection angular range. The deflection angle θm of the oscillating mirror 33 is to be explained later. The number of oscillations of the oscillating mirror 33 is set in correspondence to the length of time required to take in a single image at the image-capturing element 26 of the light-receiving optical system 14 (the shutter speed).

Figure 9:
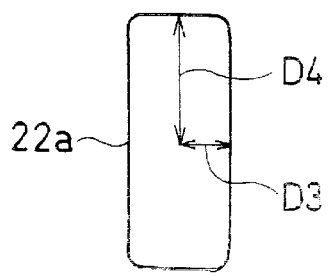
FIG. 9 illustrates the size of the pupil of the illumination optical system 13.

The end surface 22a of the light guide 22 which is caused to undergo deflection scanning linearly by the oscillating mirror 33 of the afocal scanning system 31 has a rectangular shape as shown in FIG. 9, and its radius D3 along the scanning direction is smaller than the radius D4 along the direction perpendicular to the scanning direction.

Figure 10A:
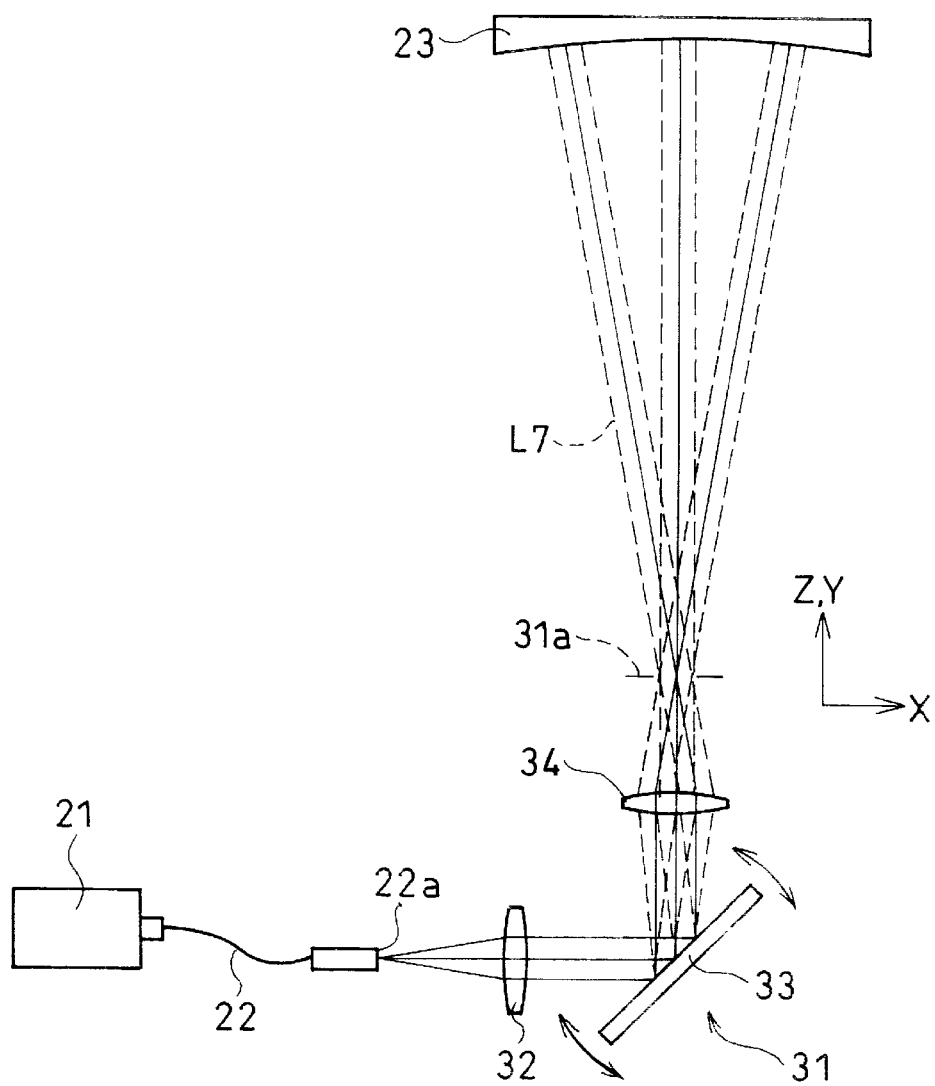
FIG. 10 illustrates linear scanning performed by the afocal scanning system.
Figure 10B:
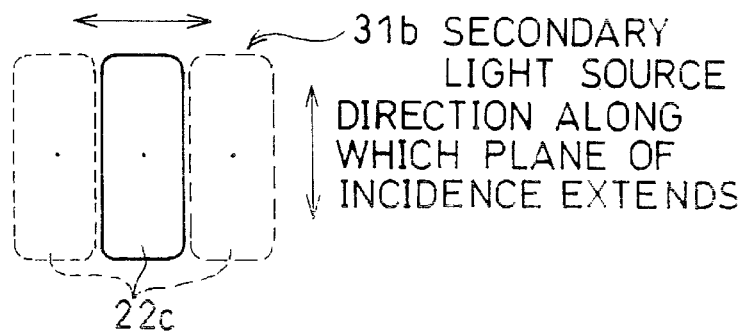

When the end surface 22a of the light guide 22 is linearly scanned by engaging the oscillating mirror 33 of the afocal scanning system 31, an image 22c of the end surface 22a of the light guide 22 makes linear reciprocal movement within the focal plane 31a of the concave reflecting mirror 23 in correspondence to the movement of the oscillating mirror 33, as shown in FIGS. 10(a) and 10(b).

The image 22c moves (is scanned) at the focal plane 31a of the concave reflecting mirror 23 along a direction perpendicular to the plane of incidence (the YZ plane). Thus, a secondary light source 31b is formed on the focal plane 31a of the concave reflecting mirror 23.

In this defect inspection apparatus 30, the secondary light source 31b formed on the focal plane 31a of the concave reflecting mirror 23 constitutes the pupil of the illumination optical system 13. The secondary light source 31b is conjugate with the aperture 25a of the lens 25 at the light-receiving optical system 14.

A light flux L7 from the secondary light source 31b enters the concave reflecting mirror 23, where it is reflected to become a roughly parallel light flux (illuminating light L8) which is then irradiated on the wafer 11 (see FIG. 8).

Figure 11:
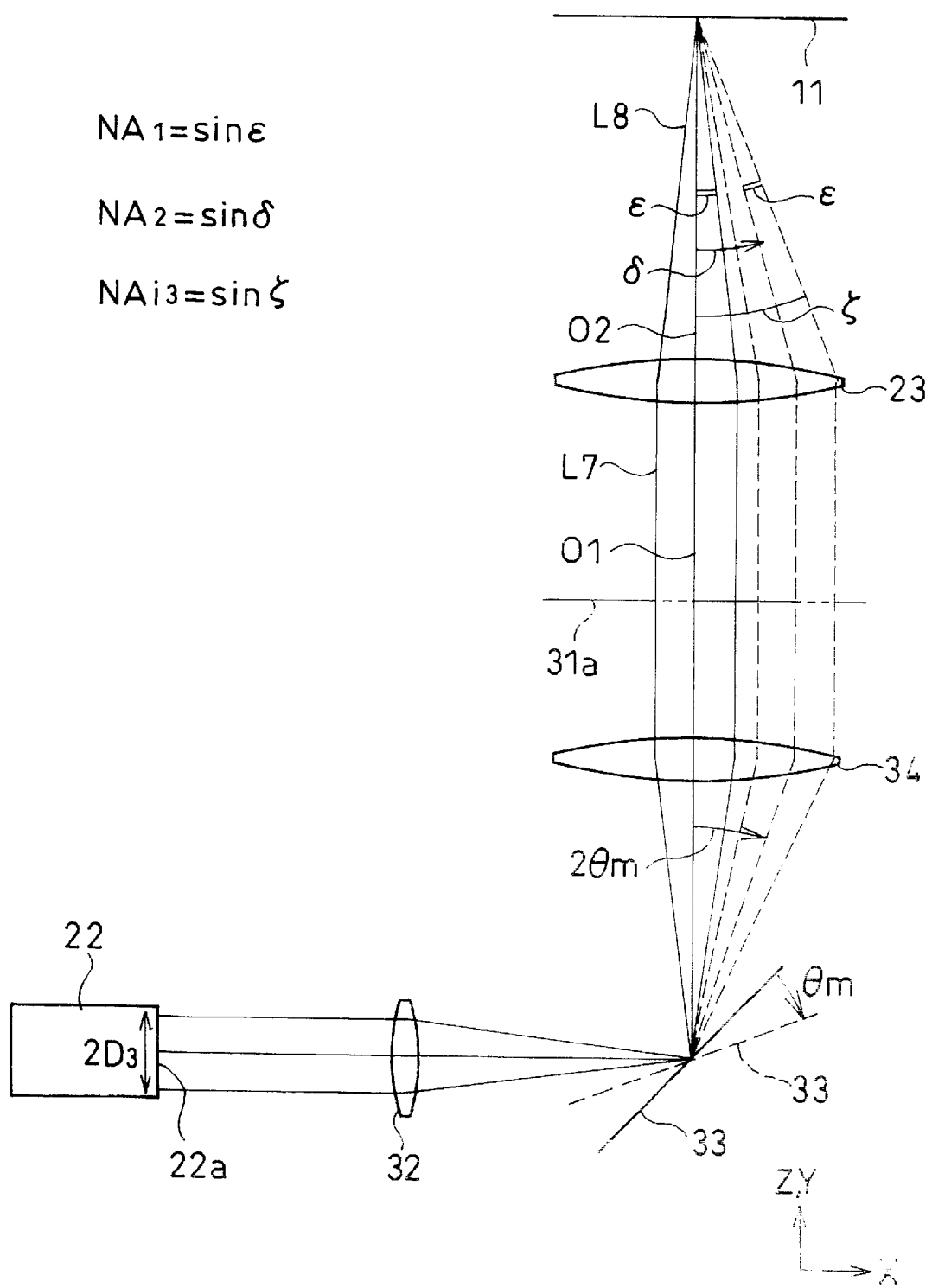
FIG. 11 illustrates an increase in the numerical aperture achieved by the afocal scanning system.
Figure 12:
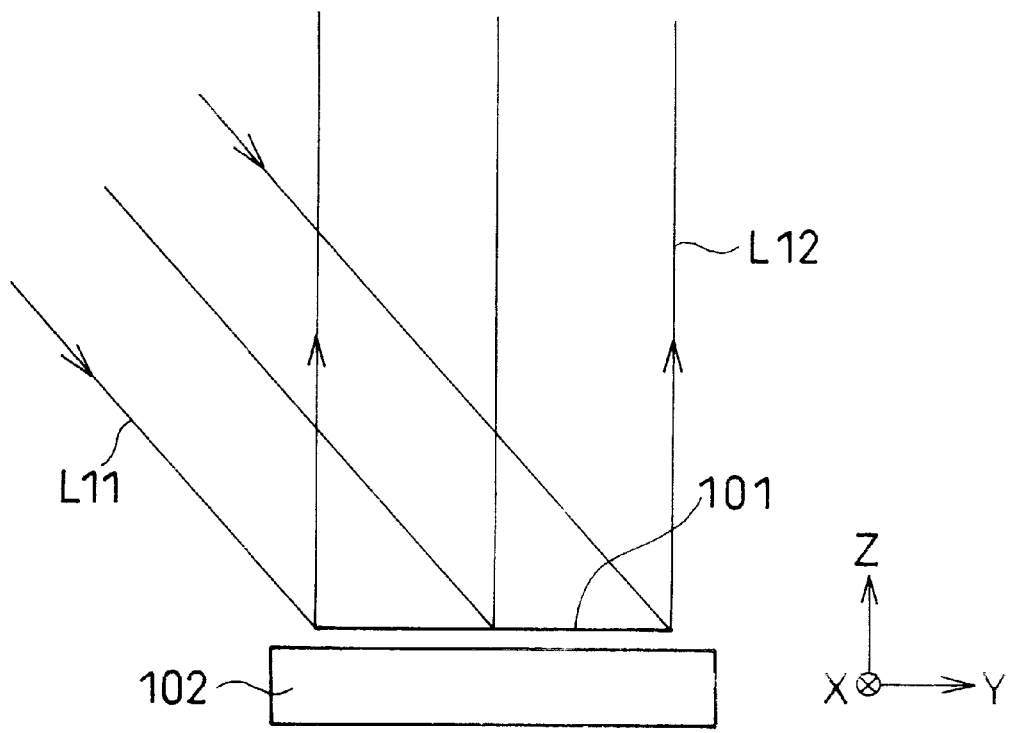
FIG. 12 illustrates defect inspection in the prior art.
Figure 12:
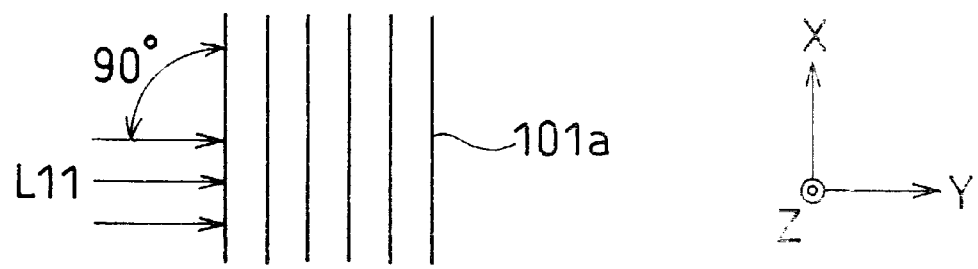

Along the direction perpendicular to the plane of incidence, a numerical aperture (a numerical aperture NAi3) of the illumination optical system 13 on the wafer 11 is set larger than a numerical aperture NA1 which is determined solely in correspondence to the size D3 of the end surface 22a, as illustrated in FIG. 11, through the linear scanning operation performed by the afocal scanning system 31. The numerical aperture NAi3 changes in correspondence to the deflection angle θm of the oscillating mirror 33.

The numerical aperture NAi3 at the illumination optical system 13 along the direction perpendicular to the plane of incidence is expressed (see expression (43)) as the total of the numerical aperture NA1 (see expression (41)) achieved when the oscillating mirror 33 is not oscillating and the increase NA2 (see expression (42)) in the numerical aperture resulting from oscillation of the oscillating mirror 33.

$$NA1 = D3 \cdot \frac{f5}{f3} \cdot \frac{1}{f6} \quad (41)$$

$$NA2 = f5 \cdot \tan 2\theta m \cdot \frac{1}{f6} \quad (42)$$

$$NAi3 = NA1 + NA2 \quad (43)$$

In expression (41) and (42), D3 represents the radius of the end surface 22a of the light guide 22 along the scanning direction, f3 represents the focal length of the lens 32, f5 represents the focal length of the lens 34, f6 represents the focal length of the concave reflecting mirror 23 and θm represents the deflection angle of the oscillating mirror 33 (on one side of the optical axis O).

A numerical aperture NAi4 at the illumination optical system 13 along the direction parallel to the plane of incidence (the non-scanning direction) is expressed as in the following expression (44), similar to the numerical aperture NA1 (see expression (41)), with D4 representing the radius of the end surface 22a of the light guide 22 along the non-scanning direction.

$$NAi4 = D4 \cdot \frac{f5}{f3} \cdot \frac{1}{f6} \quad (44)$$

Figure 2B:
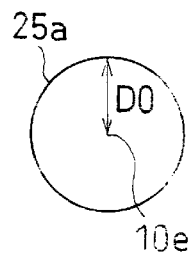

Since the light-receiving optical system 14 in the second embodiment is structured identical to that in the defect inspection apparatus 10 (see FIGS. 1 and 2(b)), the numerical apertures at the light-receiving optical system 14 are expressed as in the mathematical expression (14) explained earlier. Thus, as long as the numerical apertures NAi3 and NAi4 at the illumination optical system 13 satisfy the following equations (45) and (46), the quantity of the diffracted light L5 (see FIG. 8) passing through the pupil (the aperture 25a of the lens 25) of the light-receiving optical system 14 can be sustained at a constant level even when a diffraction angle offset of the diffracted light L3 manifests.

$$NAi3 - NAo2 = d\theta drm + k \quad (45)$$

$$NAi4 - NAo1 = d\theta drm + k \quad (46)$$

It is to be noted that the rotational angle offset quantity dθr is normally larger than the tilt angle offset quantity dθt, since the rotational angle offset quantity dθr is the sum of the error occurring when the wafer 11 is placed on the inspection stage 12 and the error of the shot coordinates relative to the external reference at the wafer 11.

In addition, the maximum value (dθdrm) of the diffraction angle offset quantity dθdr attributable to a rotational angle offset is 1.54 times the rotational angle offset quantity dθr, the maximum value (dθdtm) of the diffraction angle offset quantity dθdt attributable to a tilt angle offset is twice the rotational angle offset quantity dθt and there are no significant differences between the values assumed for the coefficients. It is to be noted that the diffraction angle offset quantity dθdr manifests along the direction perpendicular to the plane of incidence, whereas the diffraction angle offset quantity dθdt manifests along the direction in which the plane of incidence extends.

Thus, the difference between the numerical aperture at the illumination optical system 13 and the numerical aperture at the light-receiving optical system 14 along the direction perpendicular to the plane of incidence (see expressions (35) and (45)) is normally set larger than the difference along the direction parallel to the plane of incidence (see expressions (33) and (46)).

Since linear scanning is performed along the direction perpendicular to the plane of incidence in which the difference in the numerical aperture is set larger (see expression (45)) in the defect detection inspection apparatus 30 in the second embodiment, the size of the end surface 22a of the light guide 22 can be set smaller to minimize the cost increase, compared to a structure in which scanning is performed along the direction parallel to the plane of incidence.

While an explanation is given above in reference to the second embodiment on an example in which the end surface 22a is linearly scanned, the end surface may be two dimensionally scanned instead by reducing the diameter of the light guide 22.

In addition, the differences between the numerical apertures at the illumination optical system 13 and the numerical apertures at the light-receiving optical system 14 may be set equal to or larger than the sum dθdtm+k (, dθdrm+k) of the maximum value dθdtm (, dθdrm) of the diffraction angle offset quantity dθdt (, dθdr) and the angular width k of the diffraction angle offset quantity dθdi.

What is claimed is:

1. A defect inspection apparatus comprising:
    an illumination optical system that illuminates a substrate; and
    a light-receiving optical system that receives diffracted light from the substrate to inspect for defects at the substrate based upon an image of the substrate obtained with said light-receiving optical system, wherein:
    a first numerical aperture at said illumination optical system is different from a second numerical aperture at said light-receiving optical system; and
    an absolute value of a difference between said first and second numerical apertures is set at a value equal to or greater than an angular offset quantity manifesting between a direction along which said diffracted light advances and a direction along which the optical axis of said light-receiving optical system extends.

2. A defect inspection apparatus according to claim 1, wherein:
    the absolute value of the difference between said first and second numerical apertures is set at a value equal to or greater than said angular offset quantity attributable to a rotational angle offset of the substrate relative to a normal line of the substrate along a direction perpendicular to a plane of incidence containing the optical axis of said illumination optical system and the normal line of the substrate.

3. A defect inspection apparatus according to claim 1, wherein:
    the absolute value of the difference between said first and second numerical apertures is set at a value equal to or greater than said angular offset quantity attributable to a rotational angle offset of the substrate relative to an axis perpendicular to a plane of incidence containing the optical axis of said illumination optical system and a normal line of the substrate along a direction parallel to said plane of incidence.

4. A defect inspection apparatus according to claim 2, wherein:

the absolute value of the difference between said first and second numerical apertures is set at a value equal to or greater than said angular offset quantity attributable to a rotational angle offset of the substrate relative to an axis perpendicular to a plane of incidence containing the optical axis of said illumination optical system and a normal line of the substrate along a direction parallel to said plane of incidence.

5. A defect inspection apparatus according to claim 1, wherein:

at least one of said illumination optical system and said light-receiving optical system includes at least one reflection optical system; and the absolute value of the difference between said first and second numerical apertures is set at a value equal to or greater than said angular offset quantity attributable to an aberration at said reflection optical system, along a direction parallel to an off-axis plane of said reflection optical system.

6. A defect inspection apparatus according to claim 4, wherein:

at least one of said illumination optical system and said light-receiving optical system includes at least one reflection optical system; and the absolute value of the difference between said first and second numerical apertures is set at a value equal to or greater than said angular offset quantity attributable to an aberration at said reflection optical system, along a direction parallel to an off-axis plane of said reflection optical system.

7. A defect inspection apparatus according to claim 6, wherein:

said angular offset quantity k attributable to the aberration is expressed as in expression (1) when an off-axis angle $\phi$ (rad) and a focal length $f$ (mm) of said reflection optical system and a radius R (mm) of the substrate satisfy conditions expressed as $-R/f < -0.3438\phi - 0.0025$;

$$k = k1(R/f)^3 + k2(R/f)^2 + k3(R/f) + k4 \qquad (1),$$

is expressed as in expression (2) when conditions expressed as $-R/f \geq -0.3438\phi - 0.0025$ are satisfied;

$$k = 2(k1(R/f)^3 + k3(R/f)) \qquad (2);$$

and coefficients k1, k2, k3 and k4 in expressions (1) and (2) expressing said angular offset quantity k are expressed as in expressions (3), (4), (5) and (6) respectively;

$$k1 = 0.8942\phi^2 - 0.0317\phi + 0.1312 \qquad (3)$$

$$k2 = 0.4611\phi^2 + 0.7738\phi \qquad (4)$$

$$k3 = 0.5768\phi^2 - 0.0075\phi + 0.0007 \qquad (5)$$

$$k4 = 0.0903\phi^3 \qquad (6).$$

8. A defect inspection apparatus according to claim 1, wherein: the first numerical aperture is larger than the second numerical aperture.

9. A defect inspection apparatus according to claim 8, wherein:

said illumination optical system includes a means for scanning a surface set at a position conjugate with a pupil of said illumination optical system at least along a linear direction.

10. A defect inspection apparatus according to claim 7, wherein:

the first numerical aperture is larger than the second numerical aperture; and said illumination optical system includes a means for scanning a surface set at a position conjugate with a pupil of said illumination optical system at least along a linear direction.

11. A defect inspection apparatus according to claim 1, wherein:

at least one of: (i) a relative position between said substrate and said illumination optical system and (ii) a relative position between said substrate and said light-receiving optical system is changed based upon a pitch of the pattern formed at said substrate.

* * * * *